United States Patent [19]

Tsai et al.

[11] 4,442,293

[45] Apr. 10, 1984

[54] DI-ACETYLENYL-SUBSTITUTED 2-PHENYLBENZOTHIAZOLES

[75] Inventors: Tsu-Tzu Tsai, Dayton; Fred E. Arnold, Centerville, both of Ohio

[73] Assignee: The United States of America as represented by the Secretary of the Air Force, Washington, D.C.

[21] Appl. No.: 356,576

[22] Filed: Mar. 9, 1982

[51] Int. Cl.$^3$ ............................................. C07D 277/66
[52] U.S. Cl. ..................................................... 548/152
[58] Field of Search ........................................ 548/152

[56] References Cited

U.S. PATENT DOCUMENTS

| | | | |
|---|---|---|---|
| 3,816,443 | 6/1974 | Dorn | 260/304 |
| 4,147,858 | 4/1979 | Evers | 528/210 |
| 4,147,868 | 4/1979 | Arnold et al. | 544/353 |
| 4,263,461 | 4/1981 | Reinhardt et al. | 568/636 |

Primary Examiner—Paul M. Coughlan, Jr.
Assistant Examiner—D. B. Springer
Attorney, Agent, or Firm—Donald J. Singer; Charles E. Bricker

[57] ABSTRACT

Mono- and di-acetylenic-substituted 2-phenylbenzothiazoles are prepared by reacting the corresponding mono- or di-halogen-substituted 2-phenylbenzothiazole with an alkyne, such as 2-methyl-3-butyne-2-ol in the presence of a suitable catalyst.

9 Claims, No Drawings

DI-ACETYLENYL-SUBSTITUTED 2-PHENYLBENZOTHIAZOLES

RIGHTS OF THE GOVERNMENT

The invention described herein may be manufactured and used by or for the Government of the United States for all governmental purposes without the payment of any royalty.

This invention relates to acetylene-containing aromatic benzothiazole compounds.

In recent years, considerable research has been done in the area of high temperature organic polymers, especially aromatic heterocycles. Among the more thermally stable aromatic heterocycle polymers are the polybenzothiazoles.

The polybenzothiazoles have been synthesized by at least two procedures. First, a fused benzothiazole may be obtained by cyclization of an ortho-mercapto aromatic amine with an acid derivative. This can be accomplished in one step in polyphosphoric acid. Alternatively, the polybenzothiazole can be formed in two steps, the first being condensation to the polyamide in solution, and the second being cyclization of the precursor. Second, the benzothiazole nucleus may be formed prior to polymerization. The latter procedure is disadvantageous because no easily soluble prepolymer is available. A disadvantage common to both of these procedures is that the reaction during curing may produce one or more undesirable by-products, such as an off-gas. What is desired is a polymerization system which will provide a thermally stable polymer, which is easily processable prior to polymerization and which does not produce by-products during polymerization or during post-curing.

We have prepared a series of compounds that can be thermally polymerized to form thermally stable benzothiazole polymers.

Accordingly, it is an object of this invention to provide novel acetylenic-substituted 2-phenylbenzothiazoles.

It is another object of this invention to provide a method for making acetylenic-substituted 2-phenylbenzothiazoles.

Other objects and advantages of the present invention will become apparent to those skilled in the art from a reading of the following disclosure.

In accordance with the present invention there is provided a new compound having the general formula

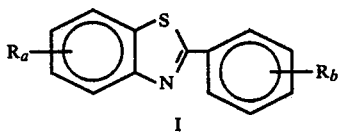

wherein $R_a$ and $R_b$ are —H or C≡CH, and wherein at least one of $R_a$ or $R_b$ is —C≡CH.

The compounds of this invention are prepared by reacting the corresponding mono- or di-halogen-substituted 2-phenylbenzothiazole with an alkylene such as 2-methyl-3-butyne-2-ol or ethynyltrimethyl silane in the presence of a catalytic amount of a suitable catalyst. In the case of 2-methyl-3-butyne-2-ol, the reaction involved can be represented by the following:

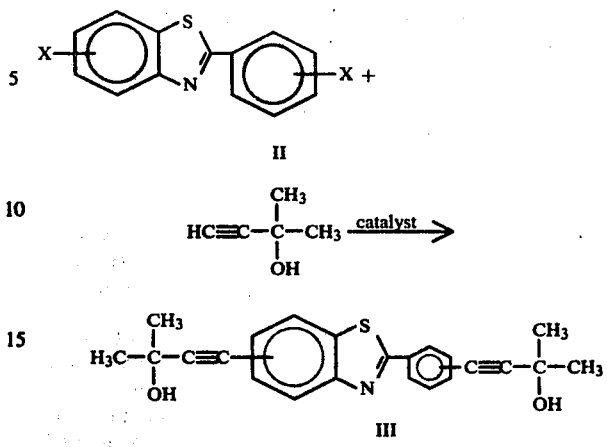

The adduct III may be mono- or di-substituted, depending upon the degree of substitution of the starting mono- or di-halogen-substituted 2-phenylbenzothiazole. Displacement of acetone by hydrolysis of the mono- or di-butynol adduct III provides the compounds I, as represented by the following

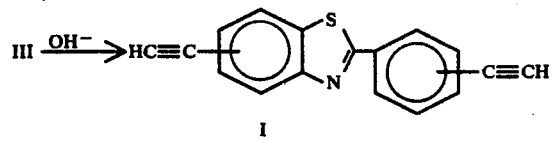

The mono- or di-halogen-substituted 2-phenylbenzothiazole (II) can be prepared by reacting an o-amino-thiophenol with a benzoic acid. One or both of the reactants may be mono-halogen-substituted, the reaction involved can be represented by the following

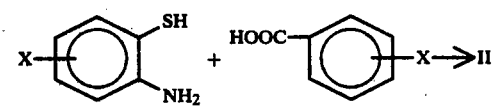

where x represents -F, -I, or, preferably, -Br.

The reaction of an appropriate o-aminothiophenol with an appropriate benzoic acid may be carried out in polyphosphoric ester and an inert organic solvent such as chloroform, toluene, benzene, or the like, at moderate temperature for 1–3 hours, or it may be carried out in polyphosphoric acid at elevated temperatures (e.g., 200° C.) to yield the corresponding mono- or di-halogen-substituted 2-phenylbenzothiazole.

Treatment of the mono- or di-halogen-substituted 2-phenylbenzothiazole with the acetylenic compound may be carried out in a suitable solvent in the presence of a suitable catalyst. In the case of 2-methyl-3-butyn-2ol, the solvent may be a basic solvent, such as triethylamine, diethylamine, or the like, including mixtures of these solvents with dimethylacetamide. A suitable catalyst mixture for this reaction includes triphenylphosphine palladium (II) dichloride, triphenylphosphine and cuprous iodide, in a ratio, by weight, ranging from 1:5:2 to 1:10:5, respectively. The amount of this catalyst mixture can range from about 1 to about 10 percent, preferably about 2 to 5 percent, by weight, based upon the weight of the substituted 2-phenylbenzothiazole reactant. The reaction is carried out in an inert atmosphere at a temperature in the approximate range of 75°–100° C. for a period of about 12 to 36 hours. The acetylenic compound is employed in excess, generally from about 1.5 to about 2.5 times the amount required to replace the replaceable halogen in the 2-phenylbenzothiazole compound.

The adduct III is converted to the acetylene-containing compound I by hydrolysis with a strong base, such as potassium hydroxide, sodium hydroxide, lithium hydroxide, or the like, in a suitable solvent, such as toluene. The reaction is carried out in an inert atmosphere under reflux conditions for a period of about 1 to 10 hours.

The acetylene-containing 2-phenylbenzothiazole compounds of this invention can be thermally homopolymerized by heating the monomers in an inert or oxidative atmosphere at a temperature ranging from about 200° to 380° C. A heating period of from about 1 to 2 hours is usually sufficient to obtain a complete cure although longer times, e.g., up to 24 hours, can be used.

While it is not intended to be limited to any particular theory, in the curing step it is believed that the terminal ethynyl groups propagate to form polyenes. In the case of the mono-acetylenic compounds, B—C≡CH, where B represents a mono-substituted 2-phenylbenzothiazole group, the polymer is believed to be a linear polyene having the general structure

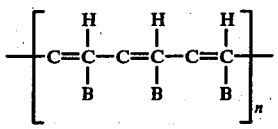

wherein n has a value of about 1 to 50.

In the case of the di-acetylenic compounds, HC≡C—B'—C≡CH, where B' represents a di-substituted 2-phenylbenzothiazole group, the resulting polymer is believed to have a polyene network, as follows

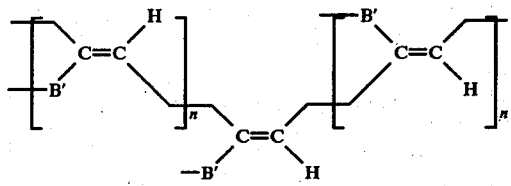

wherein each n has a value in the range of 1 to 10.

The diacetylenic compounds may also be polymerized in admixture with the monoacetylenic compounds, the latter acting as a diluent for the former.

The following examples illustrate the invention.

EXAMPLE I

Preparation of 2-(4-bromophenyl)-5-bromobenzothiazole

A mixture of 20 g (0.083 mole) of 4-bromo-2-aminothiophenol hydrochloride and 270 g of deoxygenated polyphosphoric acid was heated at 70° C. for 4 hours. To this mixture was added a solution containing 22 g (0.11 mole) of p-bromobenzoic acid dissolved in 109 g of sulfolane. The reaction mixture was slowly heated to 200° C. and maintained at that temperature for 1 hour. After cooling, the reaction mixture was poured into a 1:1 water-methanol solution to precipitate the product. The light tan precipitate was filtered, washed with dilute ammonium hydroxide, washed with water, and then air dried. The 2-(4-bromophenyl)-5-bromobenzothiazole was recrystallized from toluene to give 24.5 g (80% of theoretical), m.p. 162°–163° C.

Analysis: Calc'd for $C_{13}H_7NSBr$: C,-2.30; H,1.90; N,3.90. Found: C,42.2; H,1.56; N,3.81.

EXAMPLE II

Preparation of 2-(4-Ethynylphenyl)-5-ethynylbenzothiazole

A mixture of 28 g (0.078 mole) of 2-(4-bromophenyl)-5-bromobenzothiazole, 0.09 g of triphenylphosphine palladium II dichloride, 0.7 g of triphenylphosphine, 0.26 g of cuprous iodide and 250 ml of triethylamine was degassed by passing nitrogen through the system for 20 minutes. To the degassed mixture was added 28 g (0.33 mole) of 2-methyl-3-butyne-2ol. The reaction mixture was heated to 90° C. and maintained at that temperature for 24 hours. After cooling, the precipitated amine hydrobromide was removed by filtration. The filtrate was evaporated under reduced pressure leaving a brown solid. The solid was then dissolved in chloroform. The chloroform solution was washed with a 10% sulfuric acid solution, then with water, and thereafter dried over anhydrous magnesium sulfate. The chloroform was removed under reduced pressure, yielding 27 g (100% of theoretical) of the bisbutynol adduct which was used without purification.

A mixture of 27 g (0.078 mole) of the bis-butynol adduct dissolved in 250 ml of toluene and 2.0 g of powdered potassium hydroxide was heated to reflux. The progress of the reaction was monitored by thin layer chromatography. After about 4 hours, all the starting material was hydrolyzed. The reaction mixture was filtered and the toluene was removed under reduced pressure. The residue was eluted through a silica gel column using methylene chloride as the eluant. Removal of the eluant provided 18.4 g (91% of theoretical) of pure product: m.p. 150°–161° C.

Analysis Calc'd for $C_{17}H_9SN$: C.78.74; H,3.50; N,5.40; S,12.36. Found: C,78.43; H,2.91; N,5.07; S,12.03.

EXAMPLE III

Using the procedures given in Examples I and II, a series of mono- and diacetylenic compounds were prepared. The melting points and elementary analyses of these compounds are given in Table I below.

TABLE I

|  | m.p. °C. | Elemental Analysis | | | |
|---|---|---|---|---|---|
|  |  | C, % | H, % | N, % | S, % |
| Mono-Acetylenic Compound | | | | | |
| (Calc'd for $C_{15}H_9NS$) | — | (76.56) | (3.85) | (5.95) | (13.63) |
| 2-(3-ethynylphenyl)-benzothiazole | 87 | 77.93 | 4.46 | 6.70 | 14.32 |

TABLE I-continued

| | m.p, °C. | Elemental Analysis | | | |
|---|---|---|---|---|---|
| | | C, % | H, % | N, % | S, % |
| 2-(4-ethynylphenyl)benzothiazole | 124 | 77.27 | 3.72 | 5.57 | 13.20 |
| 2-phenyl-5-ethynylbenzothiazole | 115 | 76.57 | 3.57 | 5.28 | 13.61 |
| 2-phenyl-6-ethynylbenzothiazole | 117 | 76.65 | 3.29 | 5.71 | 13.26 |
| Di-Acetylenic Compounds | | | | | |
| (Calc'd for $C_{17}H_9NS$) | | (78.73) | (3.50) | (5.40) | (12.36) |
| 2-(4-ethynylphenyl)-5-ethynylbenzothiazole | 154 | 78.43 | 2.91 | 5.07 | 12.03 |
| 2-(3-ethynylphenyl)-5-ethynylbenzothiazole | 169 | 78.00 | 2.85 | 5.02 | 11.49 |
| 2-(4-ethynylphenyl)-5-ethynylbenzothiazole | >150 | 78.56 | 2.78 | 5.59 | 11.38 |
| 2-(3-ethynylphenyl)-6-ethynylbenzothiazole | 185 | 78.42 | 2.99 | 5.22 | 11.93 |

EXAMPLE IV

Polymerization of Mono-Acetylenic Compounds

The four mono-acetylenic 2-phenylbenzothiazole compounds prepared as in Examples II and III were thermally homopolymerized by heating samples of each compound under a blanket of nitrogen for a period ranging from 1 to 2 hours. The polymerization temperature, Tp, was determined by differential scanning calorimetry (DSC) at a heating rate of 10° C./min. The glass transition temperature, Tg, was determined by thermal mechanical analysis (TMA) at a heating rate of 10° C./min following curing of each polymer at 316° C. for 6 hours under a nitrogen atmosphere. The data obtained are shown below in Table II.

TABLE II

Thermomechanical Properties of Polymers Derived from Mono-Acetylenic Monomers

| Monomers | m.p., °C. | Tp, On-Set (°C.) | Tp, maximum (°C.) | Tg, (°C.) |
|---|---|---|---|---|
| 2-(3-ethynylphenyl)-benzothiazole | 87 | 175 | 246 | 148 |
| 2-(4-ethynylphenyl)-benzothiazole | 124 | 135 | 210 | 140 |
| 2-phenyl-5-ethynyl-benzothiazole | 115 | 150 | 224 | 172 |
| 2-phenyl-6-ethynyl-benzothiazole | 117 | 125 | 204 | 192 |

EXAMPLE V

Polymerization of Di-Acetylenic Compounds

The four di-acetylenic 2-phenylbenzothiazole compounds prepared as in Examples II and III were thermally homopolymerized as described in Example IV. The data obtained are shown below in Table III.

TABLE III

Thermomechanical Properties of Polymers Derived from Di-Acetylenic Monomers

| Monomer | m.p., °C. | Tp, On-Set (°C.) | Tp, maximum (°C.) | Tg, (°C.) |
|---|---|---|---|---|
| 2-(4-ethynylphenyl)-5-ethynylbenzothiazole | 154 | 158 | 197 | 377 |
| 2-(3-ethynylphenyl)-5-ethynylbenzothiazole | 169 | 175 | 214 | 344 |
| 2-(4-ethynylphenyl)6-ethynylbenzothiazole | >150 | 150 | 203 | 307 |
| 2-(3-ethynylphenyl)-6-ethynylbenzothiazole | 185 | 190 | 207 | 339 |

It will be evident to those skilled in the art that modifications of the present invention can be made in view of the foregoing disclosure without departing from the spirit and scope of the invention.

We claim:

1. A compound of the formula

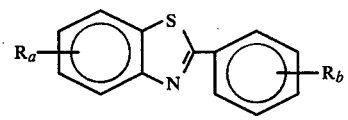

wherein $R_a$ and $R_b$ are —H or —C≡CH, wherein at least one of $R_a$ or $R_b$ is —C≡CH and wherein the location of $R_a$ is −5 or −6 and the location of $R_b$ is −3' or −4'.

2. The compound of claim 1 wherein $R_a$ is —H and $R_b$ is 3-ethynyl.

3. The compound of claim 1 wherein $R_a$ is —H and $R_b$ is 4-ethynyl.

4. The compound of claim 1 wherein $R_a$ is 5-ethynyl and $R_b$ is —H.

5. The compound of claim 1 wherein $R_a$ is 6-ethynyl and $R_b$ is —H.

6. The compound of claim 1 wherein $R_a$ is 5-ethynyl and $R_b$ is 3-ethynyl.

7. The compound of claim 1 wherein $R_a$ is 5-ethynyl and $R_b$ is 4-ethynyl.

8. The compound of claim 1 wherein $R_a$ is 6-ethynyl and $R_b$ is 3-ethynyl.

9. The compound of claim 1 wherein $R_a$ is 6-ethynyl and $R_b$ is 4-ethynyl.

* * * * *